(12) United States Patent
Koga et al.

(10) Patent No.: US 7,098,022 B2
(45) Date of Patent: Aug. 29, 2006

(54) FAMILY 19 CLASS IV CHITINASE GENE FROM YAM

(75) Inventors: Daizo Koga, Yamaguchi (JP); Takuji Mitsunaga, Yamaguchi (JP); Youzi Omura, Izumo (JP); Sadaki Kikkawa, Izumo (JP); Tomoko Kuya, Matsue (JP); Ichinari Yamamoto, Izumo (JP)

(73) Assignee: San-In Kensetsu Kougyou Co., Ltd., (JP)

( * ) Notice: Subject to any disclaimer, the term of this patent is extended or adjusted under 35 U.S.C. 154(b) by 457 days.

(21) Appl. No.: 10/374,534

(22) Filed: Feb. 26, 2003

(65) Prior Publication Data

US 2003/0175932 A1    Sep. 18, 2003

(30) Foreign Application Priority Data

Mar. 1, 2002  (JP) ............................. 2002-055222

(51) Int. Cl.
| | |
|---|---|
| C12N 15/56 | (2006.01) |
| C12N 1/19 | (2006.01) |
| C12N 1/21 | (2006.01) |
| C12N 15/63 | (2006.01) |
| C12N 9/42 | (2006.01) |

(52) U.S. Cl. ............... 435/252.3; 435/209; 435/325; 435/252.33; 435/252.31; 435/320.1; 435/254.21; 536/23.2

(58) Field of Classification Search ............ 435/209, 435/325, 252.3, 252.33, 252.31, 320.1, 254.21; 536/23.2
See application file for complete search history.

(56) References Cited

FOREIGN PATENT DOCUMENTS

JP    2000-109405    4/2000

OTHER PUBLICATIONS

D. Koga et al. "Genomic DNA Encoding Yam Chitinase", Advances in Chitin Science 3:170-177. (1998).*

T. Mitsunaga et al. "A Genomic DNA of Yam Family 19 Chitinase" Advances in Chitin Science 5:379-384. (2002).*

GenBank Accession No. AB102714. (Feb. 6, 2003).*

Tomohiro Araki, et al.,; "The Complete Amino Acid Sequence of Yam (*Dioscorea japonica*) Chitinase", *The Journal of Biological Chemistry*, vol. 262, No. 28, pp. 19944-19947 (1992).

Tomohiro Araki, et al.,; "Positions of Disulfide Bonds n Yams (*Dioscorea japonica*) Acidic Class IL (Class IV) Chitinase", *Archives of Biochemistry and Biophsics*, vol. 335, No. 1, pp. 118-122 (1996).

PCT/ISA 210 International Search Report.

Yasuyuki Arakane et al., "Comparison of Chitinase Isozymes from Yam Tuber—Enzymatic Factor Controlling the Lytic Activity of Chitinases", *Bioscience, Biotechnology and Biochemistry*, vol. 64, No. 4, pp. 723-730 (2000).

English translation of International Preliminary Examination Report, Nov. 26, 2003, Application PCT/JP2003/002223.

Tomohiro Araki, eta l., "The Complete Amino Acid Sequence of yam (*Diocorea japonica*) Chitinase", The Journal of Biological Chemistry, vol. 267, No. 28 pp. 129944-19947, (1992).

Shuji Karasuda et al., "Plant Chitinase as a Possible Biocontrol Agent for use Instead of Chemical Fungicides", Biosci, Biotechnol, Biochem, 67(1), pp. 221-224 (2003).

Takuji Mitsunaga et al., "Molecular Cloing of a Genomic DNA Encoding Yam Class IV Chitinase", Biosci, Biotechnol, Biochem., 68(7), pp. 1508-1517 (2004).

Takuji Mitsunaga et al., "Intracellular Localization of a Class IV Chitinase from Yam," Biosci, Biotechnol. Biochem, 68(7), pp. 1518-1524 (2004).

European Search Report dated Aug. 8, 2005, which issued during prosecution of International Application No. 03743516.1.

* cited by examiner

Primary Examiner—Rebecca Prouty
(74) Attorney, Agent, or Firm—Finnegan, Henderson, Farabow, Garrett & Dunner, L.L.P.

(57) ABSTRACT

The present invention provides a chitinase that can be used as a disease control agent for plants, as well as a gene encoding the chitinase. A family 19 chitinase isolated from yam and a gene encoding the chitinase are disclosed.

10 Claims, 1 Drawing Sheet

Fig. 1

```
                        CTC ATC AAT TTC CAG CCA CTC AAT TTG CAT TTA GAC ATG CAT  -301
GTG TGA CTA TAT CAG TTT CAG ATC TTT TAA TTT GTA TTT TTT TTC TTT TTC ATT TAA ATT  -241
AAA TTA AAT TCA GCT TTC AGC TTT ACA TGC ACA CAT GTG TAT TAT TTT AAT TAA TGT ACT  -181
ATG AAA TTA AGT GGG ACC CTT CAA ACC ATA CCA TAA TTA ATA TAA TAC AAA GAA GAT AAG  -121
CTC AAC GAA AGA TGA GTC ACA GAA GAG GAC AGA AGT AAC ATT GCT ATA AAT ACG CTC CGT   -61
TCT CCA TTC AAA ACC TTC ACA ACA AAG AAA AAA AAA CAA GAA GTA CTA GTA ATT AAG AAT    -1
ATG CAT TCA TTT AGA ATG ATA TTC CTT GAA GCT CTC CTC ATC GCC GGA GTT CTC TCC GGT    60
Met His Ser Phe Arg Met Ile Phe Leu Glu Ala Leu Leu Ile Ala Gly Val Leu Ser Gly
|→Signal sequence
CTC TTC TCC AGC TCT GCC GTG GCA CAA AAC TGC CAG TGC GAC ACC ACC ATC TAC TGC TGC   120
Leu Phe Ser Ser Ser Ala Val Ala Gln Asn Cys Gln Cys Asp Thr Thr Ile Tyr Cys Cys
                   S.seq←||→Chitin binding domain
AGC CAG CAT GGC TAC TGC GGC AAC AGC TAC GAC TAT TGT GGA CCG GGA TGC CAA GCC GGT   180
Ser Gln His Gly Tyr Cys Gly Asn Ser Tyr Asp Tyr Cys Gly Pro Gly Cys Gln Ala Gly
CCT TGT TTG GTT CCT TGC GAA GGA AAC GGC ACC TTA ACA GTT AGT GAT ATT GTA ACA CAG   240
Pro Cys Leu Val Pro Cys Glu Gly Asn Gly Thr Leu Thr Val Ser Asp Ile Val Thr Gln
                   Chitin binding domain←||→Catalytic domain
GAC TTT TGG GAC GGA ATT GCA TCA CAA GCC GCT GCC AAC TGT TCC GGT AAA GGC TTC TAC   300
Asp Phe Trp Asp Gly Ile Ala Ser Gln Ala Ala Ala Asn Cys Ser Gly Lys Gly Phe Tyr
ACC CTG TCT GCC TTC TTA GAA GCC GTT TCG GCT TAC CCT GGC TTT GGC ACC AAA TGC ACC   360
Thr Leu Ser Ala Phe Leu Glu Ala Val Ser Ala Tyr Pro Gly Phe Gly Thr Lys Cys Thr
GAC GAA GAC AGA AAG AGA GAG ATT GCA GCT TAC TTC GCC CAT GTC ACC CAT GAA ACT GGA   420
Asp Glu Asp Arg Lys Arg Glu Ile Ala Ala Tyr Phe Ala His Val Thr His Glu Thr Gly
                                                                Catalytic domain←
CGTACGT ACA TTT ATT CAT TCA TTC ATG CAT GCA TCT CAA TTA TAT ATA TAT AGT TCA TGA   481
||→intron
GAT ATA TAA TAT AAT ATG AGA GAT GAA ATG CTA AAG AAT TGT TTG GCT TTG TTC CGG TTA   541
ATA GAT TTA TGT TAC ATT GAA GAA AGA GAT GGA CAC GCT AAT AAC TAC TGT CTA GAA AGC   601
         His Leu Cys Tyr Ile Glu Glu Arg Asp Gly His Ala Asn Asn Tyr Cys Leu Glu Ser
intron|→Catalytic domain
CAA CAG TAT CCA TGC AAT CCT AAC AAG GAG TAC TTC GGA CGT GGA CCT ATG CAG CTC TCA   661
Gln Gln Tyr Pro Cys Asn Pro Asn Lys Glu Tyr Phe Gly Arg Gly Pro Met Gln Leu Ser
TGG AAC TAC AAC TAC ATC GAC GCC GGC AAG GAG CTC AAC TTC GAC GGC TTG AAT GAT CCG   721
Trp Asn Tyr Asn Tyr Ile Asp Ala Gly Lys Glu Leu Asn Phe Asp Gly Leu Asn Asp Pro
GAC ATA GTC GGC CGT GAC CCC ATC CTC TCC TTC AAG ACT TCT CTC TGG TAT TGG ATA AGG   781
Asp Ile Val Gly Arg Asp Pro Ile Leu Ser Phe Lys Thr Ser Leu Trp Tyr Trp Ile Arg
AAA GGG GTG CAA TAC GTC ATA CTT GAT CCG GAC CAG GGC TTC GGA GCC AGC ATC AGA ATC   841
Lys Gly Val Gln Tyr Val Ile Leu Asp Pro Asp Gln Gly Phe Gly Ala Ser Ile Arg Ile
ATC AAC GGC GGC CAA GAG TGT GAT GGC AAG AAC ACC GCC CAG ATG ATG GCG CGT GTG GGA   901
Ile Asn Gly Gly Gln Glu Cys Asp Gly Lys Asn Thr Ala Gln Met Met Ala Arg Val Gly
TAC TAC GAG CAA TAT TGT GCC CAG CTT GGT GTC TCT CCT GGC AAT GAT CTC ACT TGT GTC   961
Tyr Tyr Glu Gln Tyr Cys Ala Gln Leu Gly Val Ser Pro Gly Asn Asp Leu Thr Cys Val
ACT AGT AAC CTG GCT GTT AGT TAG TAA GTG CAT GCA TGC ACA AGT ACG TAT GTT ACT AAA  1021
Thr Ser Asn Leu Ala Val Ser ***
              Catalytic domain←|
TCA GCG GCT ATT GAG ATG CAG CAC TGT GTG TTG TGT TTC CCT AAA TAA ATG CTG ATG ATG  1081
AAT AAC AAT GTT ATT CAT GGT GAA TAA ATT TAT CTT TAA TTA ATG GCT CCG TCT CCA TAA  1141
ATA ATC TTT GTT TTT ATC GCA GAA ACG GTT CTG AAT ATT TGG ATT TTT AAA AAT ATA ATA  1201
AAT TAA ATA TGA TAA TTT TAA TTC TAT ACA TAT TTA GTC GAG CAA ATC AAT TTG GTT AAA  1261
GTT TAT GAA CTT GGC TTA AAT TCG ACT A                                            1289
```

FAMILY 19 CLASS IV CHITINASE GENE FROM YAM

BACKGROUND OF THE INVENTION

1. Technical Field

The present invention relates to a novel chitinase from yam and a gene encoding the chitinase. This chitinase has a strong lytic activity and, thus, is useful as an agent for controlling plant pathogens.

2. Prior Art

A great number of edible or ornamental plants are cultured at present. Generally, such cultivars are weaker against pathogenic fungi and bacteria than wild-type species. Thus, it is necessary to apply large quantities of agricultural chemicals (agents for controlling plant pathogenic fungi or bacteria) for obtaining sufficient yields. As agents for controlling plant pathogenic fungi or bacteria, chemically synthesized agents of heterocyclic aromatic compound type or organic phosphate ester type have been mainly used to date. However, these chemicals not only manifest their effect on pathogenic fungi or bacteria, but they also have an adverse effect on the human body and cause the problem of residual agricultural chemicals.

Chitinase is an enzyme that hydrolyzes chitin. There are known chitinases belonging to family 18 and those belonging to family 19. It is known that chitinases are involved in the plant defense mechanism against pathogenic fungi and bacteria. Plants infected by pathogenic fungi or bacteria protect themselves by producing chitinases and degrading the pathogen with the chitinase. It is expected that, when such chitinases are applied to soils or plant bodies, they would manifest the same effect as that of the chitinases produced in the plant bodies and thus could protect the plants from infection with pathogenic fungi and/or bacteria. Since chitinases are substances produced by organisms, it can be considered that agents for controlling plant pathogens utilizing chitinases are highly safe against the human body and environments.

Several reports have already been made on the use of plant-derived chitinases as agents for controlling plant pathogens. For example, the present inventors have isolated a chitinase belonging to family 18 from yam and revealed that the chitinase exhibits control effect on pathogens such as *Pyricularia oryzae* (fungus that causes rice blast) (Japanese Unexamined Patent Publication No. 2000-109405).

The finding of a novel plant chitinase will lead to the development of novel agents for controlling plant pathogens. Besides, for efficient production of agents for controlling plant pathogens using the chitinase, it is necessary to isolate the gene encoding the chitinase.

SUMMARY OF THE INVENTION

The present invention has been made under these circumstances for the purpose of providing a novel gene encoding a plant chitinase.

As a result of intensive and extensive researches toward the solution of the above problem, the present inventors have found in yam a novel chitinase belonging to family 19 that is different from the previously found chitinase belonging to family 18. The present invention has been achieved based on this finding.

The present invention relates to a yam chitinase gene encoding the amino acid sequence as shown in SEQ ID NO: 2 or an amino acid sequence substantially identical thereto.

The present invention also relates to a yam chitinase represented by the amino acid sequence as shown in SEQ ID NO: 2 or an amino acid sequence substantially identical thereto.

BRIEF DESCRIPTION OF THE DRAWINGS

FIG. 1 is a diagram showing the amino acid sequence of the chitinase of the invention including the signal sequence, chitin binding domain and catalytic domain of the chitinase.

DESCRIPTION OF THE PREFERRED EMBODIMENT

Hereinbelow, the present invention will be described in detail.

The chitinase of the invention is represented by the amino acid sequence as shown in SEQ ID NO: 2 or an amino acid sequence substantially identical thereto; and the chitinase gene of the invention encodes the amino acid sequence as shown in SEQ ID NO: 2 or an amino acid sequence substantially identical thereto. The term "amino acid sequence substantially identical thereto" used herein means the amino acid sequence of SEQ ID NO: 2 having a mutation(s) (such as deletion, replacement or addition of one or more amino acids) that does/do not allow the represented protein to lose its function as a chitinase.

By integrating the chitinase gene of the invention into a microorganism plasmid, it is possible to express this gene in the microorganism. Such a plasmid must have at least a replication origin functional (i.e. autonomously replicating) in the host microorganism. Further, it is extremely desirable for such a plasmid to have selection marker genes which are used as markers for selecting transformants. As selection marker genes, genes that are able to confer antibiotic resistance may be used. Specific examples of well-known selection marker genes include ampicillin resistance gene and tetracycline resistance gene. Furthermore, the above-mentioned plasmid often has a promoter sequence capable of directing the expression of a constitutive gene. Alternatively, a promoter sequence may be inserted into the plasmid together with a constitutive gene. These techniques are well known in the art. One of ordinary skill in the art can select and use appropriate techniques.

Plasmids are introduced into microorganism cells and function therein. Methods for introducing plasmids into microorganism cells are well known. One of ordinary skill in the art may select and use appropriate methods from those known methods.

As host microorganisms, *Bacillus subtilis*, *Escherichia coli* and *Saccharomyces cerevisiae* are well known and used widely. In particular, *E. coli* is used frequently for the purposes of gene amplification and selection.

Specific examples of hosts such as *B. subtilis*, *E. coli* and yeast and specific examples of useful plasmids are described in a large number of documents. One of ordinary skill in the art may select and use appropriate ones from them.

Culturing a microorganism transformed with a plasmid to thereby obtain a chitinase does not need to be a special process. Briefly, the transformed microorganism is cultured in a medium where it can grow well and under conditions that allow its good growth. Subsequently, the chitinase produced in the medium, inside of the cells or around the cell membranes is recovered. Methods for isolation/purification of polypeptides such as chitinase are also well known. One of ordinary skill in the art may combine these known methods to isolate and purify the chitinase.

The thus obtained chitinase of the invention has a strong lytic activity. Therefore, this chitinase can be used as an agent for controlling plant pathogenic fungi and bacteria.

EXAMPLE (1) Determination of Partial cDNA Sequence

Yam (*Dioscorea opposita* Thunb) callus was induced from seedlings on MS agar medium (containing $10^{-4}$ M 2,4-dichlorophenoxyacetic acid [2,4-D], $10^{-5}$ M kinetin and 5% sucrose) in the presence of 0.1% activated charcoal at 27° C. in the dark. The resultant callus (about 300 mg) was treated with 50 μl of a suspension of *Fusarium oxysporum* macroconidia (0.5–1.5 mg). Total RNA was extracted from the *F. oxysporum*-inoculated callus. mRNA was separated from the total RNA by affinity chromatography using oligo dT-cellulose and then cDNA was synthesized from the mRNA. A cDNA encoding a yam chitinase was selectively amplified by polymerase chain reaction (PCR). Primers for the PCR were synthesized based on nucleotide sequences deduced from partially known amino acid sequences of chitinase. The PCR products were subcloned and sequenced.

(2) Determination of Partial Genomic DNA Sequence

Genomic DNA was extracted from yam leaves, and PCR was performed with primers synthesized based on the partial cDNA sequence. The PCR products were subcloned and sequenced.

(3) Preparation of Oligonucleotide Primers

Gene specific primers were synthesized based on the partial genomic DNA sequence. Random primers were purchased from BEX Co., Ltd. Their melting temperatures (Tms) were calculated using the following formula:

69.3+0.41(% GC)−650/L (Mazars et al., 1991) where L is primer length (Table 1).

The PCR products were purified with QIA Quick PCR Purification kit (Qiagen) and eluted with 50 μl of an elution buffer consisting of 10 mM Tris-HCl (pH 8.5).

The secondary PCR was performed in three ways using (i) a combination of 0.4 μM GSP-R2 (this primer is located at a nested position) and 0.4 μM random primer A28 (the same primer used in the primary PCR); (ii) GSP-R2 alone; or (iii) A28 alone. The reaction composition and the thermal cycling conditions were the same as in the primary PCR except that 1 μl of the primary PCR product was used as a template and that 35 cycles were reduced to 25 cycles. The PCR products were separated by 1/5% agarose gel electrophoresis. The DNA band obtained from the PCR using the primer combination of GSP-R2 and A28 was cut out from the agarose gel and purified with Geneclean II kit (BIO 101, Inc.). The purified DNA fragment was subcloned into TOPO vector, which was introduced into *E. coli* using TOPO™ TA Cloning kit (Invitrogen). Positive clones were selected by colony PCR as described below. Briefly, a colony was picked up with a sterile toothpick and swilled in 40 μl of sterile water. The colony in sterile water was transferred into a heat block pre-heated to 95° C., boiled for 10 min, placed on ice immediately and used as a template. With this template, PCR was performed in a 50 μl solution containing 0.4 μM each of GSP-F1 and GSP-R2. Other components of the reaction solution were the same as in the primary PCR. The thermal cycling conditions were set as shown below.

TABLE 1

| Primer | Sequence | Melting temp. | SEQ ID NO |
|---|---|---|---|
| Gene specific primer | | | |
| GSP-F1 | 5'-ATGGAGAACTGCCAGTGCGA-3' | 59.4 | SEQ ID NO: 3 |
| GSP-F2 | 5'-TGCAGCTTACTTCGCCCAT-3' | 56.7 | SEQ ID NO: 4 |
| GSP-F3 | 5'-CTACTGTCAAGAAAGCCAAC-3' | 55.3 | SEQ ID NO: 5 |
| GSP-F4 | 5'-GTACTTCGGACGTGGACC-3' | 58.2 | SEQ ID NO: 6 |
| GSP-F5 | 5'-CTCATCAATTTCCAGCCACTC-3' | 57.9 | SEQ ID NO: 7 |
| GSP-F6 | 5'-CGACTATTGTGGACCGGG-3' | 58.2 | SEQ ID NO: 8 |
| GSP-R1 | 5'-AACCAGAGAGAAGTCTTGAA-3' | 53.2 | SEQ ID NO: 9 |
| GSP-R2 | 5'-TGTAGAAGCTTTTACCGGGA-3' | 55.3 | SEQ ID NO: 10 |
| GSP-R3 | 5'-CATCACACTCTTGGCCGC-3' | 58.2 | SEQ ID NO: 11 |
| GSP-R4 | 5'-TAGTCGAATTTAAGCCAAGTTC-3' | 54.7 | SEQ ID NO: 12 |
| GSP-R5 | 5'-GGTCCACGTCCGAAGTAC-3' | 58.2 | SEQ ID NO: 13 |
| Random primer | | | |
| A28 | 5'-TACCCTCAAGCT-3' | 35.6 | SEQ ID NO: 14 |
| A02 | 5'-GCCAGCTGTACG-3' | 42.5 | SEQ ID NO: 15 |

(4) Cloning of the 5' Region of the Chitinase Gene

The primary PCR was carried out in a 50 μl solution containing 50 ng of genomic DNA, 0.4 μM gene specific primer (GSP-R1), 0.4 μM random primer (A28), 200 μM each of dNTPs, 1 U of Ex Taq polymerase (TAKARA BIO INC.) and 1×Ex Taq™ buffer. Thermal cycling conditions were set as shown below.

TABLE 2

| Denaturation | 94° C. × 2 min | 1 cycle |
|---|---|---|
| Denaturation | 94° C. × 1 min | 35 cycles |
| Annealing | 50° C. × 2 min | |
| Extension | 72° C. × 3 min | |
| Extension | 72° C. × 7 min | 1 cycle |

The PCR was performed with Astec Program Temp Control System PC-800.

TABLE 3

| Denaturation | 94° C. × 2 min | 1 cycle |
|---|---|---|
| Denaturation | 94° C. × 1 min | 25 cycles |
| Annealing | 56° C. × 1 min | |
| Extension | 72° C. × 1 min | |
| Extension | 72° C. × 7 min | 1 cycle |

Plasmid DNA was prepared from each of the positive clones using QIAprep Spin Miniprep kit (Qiagen) and then sequenced.

(5) Cloning of the 3' Region of the Chitinase Gene

The primary PCR was performed using 0.4 μM GSP-F2 which was used both as a gene specific primer and as a random primer. The reaction composition, the thermal cycling conditions and the purification of PCR products were the same as in the primary PCR for cloning the 5' region. The secondary PCR was performed in three ways using (i) a combination of 0.4 µM GSP-F3 (this primer is located at a nested position) and 0.4 µM random primer A02; (ii) GSP-F3 alone; or (iii) A02 alone. The reaction composition and the thermal cycling conditions were the same as in the primary PCR except that 1 µl of the primary PCR product was used as a template. The PCR products were separated by 1.5% agarose gel electrophoresis. The DNA band obtained from the PCR using the primer combination of GSP-F3 and A02 was cut out from the agarose gel and purified with Geneclean II kit (BIO 101, Inc.). The purified DNA fragment was subcloned in the same manner as described in the cloning of the 5' region. Then, positive clones were selected by the colony PCR method described in the cloning of the 5' region. This PCR was performed using 0.4 µM each of GSP-F4 and GSP-R3. The reaction composition was the same as in the primary PCR. The thermal cycling conditions were set as shown below.

TABLE 4

| Denaturation | 94° C. × 2 min | 1 cycle |
|---|---|---|
| Denaturation | 94° C. × 30 sec | 25 cycles |
| Annealing | 60° C. × 30 sec | |
| Extension | 72° C. × 30 sec | |

The preparation of plasmid DNA from positive clones and sequencing of the DNA were carried out in the same manner as in the cloning of the 5' region.

(6) Cloning of the Full-Length Yam Chitinase Gene by High Fidelity PCR

Based on the newly identified DNA sequences, gene specific primers GSP-F5, -F6, -R4 and -R5 were synthesized (Table 1). In order to isolate the full-length yam chitinase gene, high fidelity PCR was performed in a 50 µl solution containing 50 ng of genomic DNA, 0.4 µM each of GSP-F5 and GSP-R4, 200 µM each of dNTPs, 1.25 U of Pyrobest DNA polymerase (TAKARA BIO INC.) and 1× Pyrobest Buffer II. The thermal cycling conditions were set as shown below.

TABLE 5

| Denaturation | 94° C. × 2 min | 1 cycle |
|---|---|---|
| Denaturation | 94° C. × 30 sec | 25 cycles |
| Annealing | 60° C. × 1 min | |
| Extension | 72° C. × 2 min | |

PCR products were purified with QIA Quick PCR Purification kit (Qiagen) and eluted with 30 µl of an elution buffer consisting of 10 mM Tris-HCI (pH 8.5). The purified DNA fragments were subcloned in the same manner as in the cloning of the 5' region. Colony PCR was performed using 0.4 µM each of GSP-F6 and GSP-R5. The reaction composition was the same as in the primary PCR for cloning the 5' region. The thermal cycling conditions were set as shown below.

TABLE 6

| Denaturation | 94° C. × 2 min | 1 cycle |
|---|---|---|
| Denaturation | 94° C. × 30 sec | 25 cycles |
| Annealing | 60° C. × 30 sec | |
| Extension | 72° C. × 1 min | |

The preparation of plasmid DNA from positive clones and sequencing of the DNA were carried out in the same manner as described in the cloning of the 5' region. The nucleotide sequence of the full-length yam chitinase gene is shown in FIG. 1 and SEQ ID NO: 1. In addition, the amino acid sequence deduced from the nucleotide sequence is shown in SEQ ID NO: 2.

The present invention provides a yam-derived chitinase belonging to family 19 and a gene encoding the chitinase. Since this chitinase has lytic activity, it can be used as an agent for controlling plant pathogenic fungi and bacteria.

The entire disclosure of Japanese Patent Application No.2002-055222 filed on Mar. 1, 2002 including specification, claims, drawings and summary is incorporated herein by reference in its entity.

All publications, patents and patent applications cited herein are incorporated herein by reference in their entity.

What is claimed is:

1. An isolated yam chitinase gene encoding a polypeptide comprising: the amino acid sequence of SEQ ID NO: 2.

2. The yam chitinase gene according to claim 1, wherein the yam chitinase gene comprises a nucleic acid sequence of SEQ ID NO: 1.

3. A vector comprising the yam chitinase gene of claim 1.

4. An isolated recombinant host cell, comprising an expression vector, wherein the expression vector comprises:
   a nucleic acid molecule that encodes a polypepetide comprising the amino acid sequence of SEQ ID NO: 2.

5. The isolated recombinant host cell of claim 4, wherein the host cell is *Bacillus subtilis, Escherichia coli* or *Saccharomyces cerevisiae*.

6. The isolated recombinant host cell of claim 4, wherein the nucleic acid molecule comprises a nucleic acid sequence of SEQ ID NO: 1.

7. An isolated plasmid comprising a yam chitinase gene encoding a polypeptide comprising the amino acid sequence of SEQ ID NO: 2.

8. The isolated plasmid of claim 7, further comprising:
   selection marker genes used as markers for selecting transformants; and
   a promoter sequence for directing the expression of the yam chitinase gene.

9. The isolated plasmid of claim 7, wherein the yam chitinase gene comprises a nucleic acid sequence of SEQ ID NO: 1.

10. An isolated recombinant host cell comprising the plasmid of claim 7.

* * * * *

SEQUENCE LISTING

```
<160> NUMBER OF SEQ ID NOS: 15

<210> SEQ ID NO 1
<211> LENGTH: 1631
<212> TYPE: DNA
<213> ORGANISM: Dioscorea oppositifolia
<220> FEATURE:
<221> NAME/KEY: CDS
<222> LOCATION: (343)...(763)
<220> FEATURE:
<221> NAME/KEY: intron
<222> LOCATION: (764)...(887)
<220> FEATURE:
<221> NAME/KEY: CDS
<222> LOCATION: (888)...(1324)

<400> SEQUENCE: 1
ctcatcaatt tccagccact caatttgcat ttagacatgc atgtgtgact atatcagttt      60
cagatctttt aatttgtatt ttttttcttt ttcatttaaa ttaaattaaa ttcagctttc     120
agctttacat gcacacatgt gtattatttt aattaatgta ctatgaaatt aagtgggacc    180
```

-continued

| | |
|---|---|
| cttcaaacca taccataatt aatataatac aaagaagata agctcaacga aagatgagtc | 240 |
| acagaagagg acagaagtaa cattgctata aatacgctcc gttctccatt caaaaccttc | 300 | acaacaaaga aaaaaaaaca agaagtacta gtaattaaga at atg cat tca ttt  354
                                                                                                       Met His Ser Phe
                                                                                                      1 aga atg ata ttc ctt gaa gct ctc ctc atc gcc gga gtt ctc tcc ggt  402
Arg Met Ile Phe Leu Glu Ala Leu Leu Ile Ala Gly Val Leu Ser Gly
 5                       10                 15                      20 ctc ttc tcc agc tct gcc gtg gca caa aac tgc cag tgc gac acc acc  450
Leu Phe Ser Ser Ser Ala Val Ala Gln Asn Cys Gln Cys Asp Thr Thr
                   25                      30                        35 atc tac tgc tgc agc cag cat ggc tac tgc ggc aac agc tac gac tat  498
Ile Tyr Cys Cys Ser Gln His Gly Tyr Cys Gly Asn Ser Tyr Asp Tyr
                40                      45                       50 tgt gga ccg gga tgc caa gcc ggt cct tgt ttg gtt cct tgc gaa gga  546
Cys Gly Pro Gly Cys Gln Ala Gly Pro Cys Leu Val Pro Cys Glu Gly
        55                      60                      65 aac ggc acc tta aca gtt agt gat att gta aca cag gac ttt tgg gac  594
Asn Gly Thr Leu Thr Val Ser Asp Ile Val Thr Gln Asp Phe Trp Asp
 70                       75                 80 gga att gca tca caa gcc gct gcc aac tgt tcc ggt aaa ggc ttc tac  642
Gly Ile Ala Ser Gln Ala Ala Ala Asn Cys Ser Gly Lys Gly Phe Tyr
 85                       90                 95                 100 acc ctg tct gcc ttc tta gaa gcc gtt tcg gct tac cct ggc ttt ggc  690
Thr Leu Ser Ala Phe Leu Glu Ala Val Ser Ala Tyr Pro Gly Phe Gly
                105                    110                 115 acc aaa tgc acc gac gaa gac aga aag aga gag att gca gct tac ttc  738
Thr Lys Cys Thr Asp Glu Asp Arg Lys Arg Glu Ile Ala Ala Tyr Phe
                120                    125                 130 gcc cat gtc acc cat gaa act gga c gtacgtacat ttattcattc  783
Ala His Val Thr His Glu Thr Gly
             135                    140 attcatgcat gcatctcaat tatatatata tagttcatga gatatataat ataatatgag  843
agatgaaatg ctaaagaatt gtttggcttt gttccggtta atag at tta tgt tac  898
                                                                His Leu Cys Tyr att gaa gaa aga gat gga cac gct aat aac tac tgt cta gaa agc caa  946
Ile Glu Glu Arg Asp Gly His Ala Asn Asn Tyr Cys Leu Glu Ser Gln
145                    150                    155                 160 cag tat cca tgc aat cct aac aag gag tac ttc gga cgt gga cct atg  994
Gln Tyr Pro Cys Asn Pro Asn Lys Glu Tyr Phe Gly Arg Gly Pro Met
                    165                    170                 175 cag ctc tca tgg aac tac aac tac atc gac gcc ggc aag gag ctc aac  1042
Gln Leu Ser Trp Asn Tyr Asn Tyr Ile Asp Ala Gly Lys Glu Leu Asn
                180                    185                 190 ttc gac ggc ttg aat gat ccg gac ata gtc ggc cgt gac ccc atc ctc  1090
Phe Asp Gly Leu Asn Asp Pro Asp Ile Val Gly Arg Asp Pro Ile Leu
            195                    200                 205 tcc ttc aag act tct ctc tgg tat tgg ata agg aaa ggg gtg caa tac  1138
Ser Phe Lys Thr Ser Leu Trp Tyr Trp Ile Arg Lys Gly Val Gln Tyr
210                    215                    220 gtc ata ctt gat ccg gac cag ggc ttc gga gcc agc atc aga atc atc  1186
Val Ile Leu Asp Pro Asp Gln Gly Phe Gly Ala Ser Ile Arg Ile Ile
225                    230                    235                 240 aac ggc ggc caa gag tgt gat ggc aag aac acc gcc cag atg atg gcg  1234
Asn Gly Gly Gln Glu Cys Asp Gly Lys Asn Thr Ala Gln Met Met Ala
                    245                    250                 255 cgt gtg gga tac tac gag caa tat tgt gcc cag ctt ggt gtc tct cct  1282
Arg Val Gly Tyr Tyr Glu Gln Tyr Cys Ala Gln Leu Gly Val Ser Pro

|     |     |     |     |     |     |     |     |     |      |
| --- | --- | --- | --- | --- | --- | --- | --- | --- | ---- |
|     |     | 260 |     |     | 265 |     |     | 270 |      |
| ggc | aat | gat | ctc | act | tgt | gtc | act | agt | 1324 |
| Gly | Asn | Asp | Leu | Thr | Cys | Val | Thr | Ser |      |
|     |     | 275 |     |     | 280 |     |     |     |      |
| aac | ctg | gct | gtt | agt |     |     |     |     |      |
| Asn | Leu | Ala | Val | Ser |     |     |     |     |      |
|     |     | 285 |     |     |     |     |     |     |      | tagtaagtgc atgcatgcac aagtacgtat gttactaaat cagcggctat tgagatgcag 1384 cactgtgtgt tgtgtttccc taaataaatg ctgatgatga ataacaatgt tattcatggt 1444 gaataaattt atctttaatt aatggctccg tctccataaa taatctttgt ttttatcgca 1504 gaaacggttc tgaatatttg gattttaaa aatataataa attaaatatg ataattttaa 1564 ttctatacat atttagtcga gcaaatcaat ttggttaaag tttatgaact ggcttaaat 1624 tcgacta 1631

<210> SEQ ID NO 2
<211> LENGTH: 286
<212> TYPE: PRT
<213> ORGANISM: Dioscorea oppositifolia

<400> SEQUENCE: 2

Met His Ser Phe Arg Met Ile Phe Leu Glu Ala Leu Leu Ile Ala Gly
 1               5                  10                  15

Val Leu Ser Gly Leu Phe Ser Ser Ala Val Ala Gln Asn Cys Gln
            20                  25                  30

Cys Asp Thr Thr Ile Tyr Cys Cys Ser Gln His Gly Tyr Cys Gly Asn
         35                  40                  45

Ser Tyr Asp Tyr Cys Gly Pro Gly Cys Gln Ala Gly Pro Cys Leu Val
     50                  55                  60

Pro Cys Glu Gly Asn Gly Thr Leu Thr Val Ser Asp Ile Val Thr Gln
 65                  70                  75                  80

Asp Phe Trp Asp Gly Ile Ala Ser Gln Ala Ala Ala Asn Cys Ser Gly
                 85                  90                  95

Lys Gly Phe Tyr Thr Leu Ser Ala Phe Leu Glu Ala Val Ser Ala Tyr
            100                 105                 110

Pro Gly Phe Gly Thr Lys Cys Thr Asp Glu Asp Arg Lys Arg Glu Ile
        115                 120                 125

Ala Ala Tyr Phe Ala His Val Thr His Glu Thr Gly His Leu Cys Tyr
    130                 135                 140

Ile Glu Glu Arg Asp Gly His Ala Asn Asn Tyr Cys Leu Glu Ser Gln
145                 150                 155                 160

Gln Tyr Pro Cys Asn Pro Asn Lys Glu Tyr Phe Gly Arg Gly Pro Met
                165                 170                 175

Gln Leu Ser Trp Asn Tyr Asn Tyr Ile Asp Ala Gly Lys Glu Leu Asn
            180                 185                 190

Phe Asp Gly Leu Asn Asp Pro Asp Ile Val Gly Arg Asp Pro Ile Leu
        195                 200                 205

Ser Phe Lys Thr Ser Leu Trp Tyr Trp Ile Arg Lys Gly Val Gln Tyr
    210                 215                 220

Val Ile Leu Asp Pro Asp Gln Gly Phe Gly Ala Ser Ile Arg Ile Ile
225                 230                 235                 240

Asn Gly Gly Gln Glu Cys Asp Gly Lys Asn Thr Ala Gln Met Met Ala
                245                 250                 255

Arg Val Gly Tyr Tyr Glu Gln Tyr Cys Ala Gln Leu Gly Val Ser Pro
            260                 265                 270

Gly Asn Asp Leu Thr Cys Val Ser Asn Leu Ala Val Ser
        275                 280                 285

```
<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
atggagaact gccagtgcga                                             20

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
tgcagcttac ttcgcccat                                              19

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ctactgtcaa gaaagccaac                                             20

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
gtacttcgga cgtggacc                                               18

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
ctcatcaatt tccagccact c                                           21

<210> SEQ ID NO 8
<211> LENGTH: 18
<212> TYPE: DNA
<213> ORGANISM: Artificial Sequence
<220> FEATURE:
<223> OTHER INFORMATION: primer

<400> SEQUENCE: 8
cgactattgt ggaccggg                                               18

<210> SEQ ID NO 9
<211> LENGTH: 20
<212> TYPE: DNA
<213> ORGANISM: Artificial Sequence
<220> FEATURE:
```

```
<223> OTHER INFORMATION: primer

<400> SEQUENCE: 9
aaccagagag aagtcttgaa                                              20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tgtagaagct tttaccggga                                              20

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
catcacactc ttggccgc                                                18

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
tagtcgaatt taagccaagt tc                                           22

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
ggtccacgtc cgaagtac                                                18

<210> SEQ ID NO 14
<211> LENGTH: 12
<212> TYPE: DNA
<213> ORGANISM: Artificial Sequence
<220> FEATURE:
<223> OTHER INFORMATION: primer

<400> SEQUENCE: 14
taccctcaag ct                                                      12

<210> SEQ ID NO 15
<211> LENGTH: 12
<212> TYPE: DNA
<213> ORGANISM: Artificial Sequence
<220> FEATURE:
<223> OTHER INFORMATION: primer

<400> SEQUENCE: 15
gccagctgta cg                                                      12
```